(12) United States Patent
Ionkin

(10) Patent No.: US 8,153,794 B2
(45) Date of Patent: Apr. 10, 2012

(54) CATALYSTS USEFUL FOR CATALYZING THE COUPLING OF ARYLHALIDES WITH ARYLBORONIC ACIDS

(75) Inventor: Alex Sergey Ionkin, Kennett Square, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 798 days.

(21) Appl. No.: 12/244,935

(22) Filed: Oct. 3, 2008

(65) Prior Publication Data

US 2009/0054650 A1   Feb. 26, 2009

Related U.S. Application Data

(62) Division of application No. 11/013,679, filed on Dec. 16, 2004, now Pat. No. 7,449,601.

(51) Int. Cl.
*C07F 7/02* (2006.01)
*C07D 213/04* (2006.01)

(52) U.S. Cl. ........ 546/14; 546/346; 546/284.1; 546/144

(58) Field of Classification Search .......... 546/14, 546/144, 346, 284.1
See application file for complete search history.

(56) References Cited

U.S. PATENT DOCUMENTS

| | | | | |
|---|---|---|---|---|
| 2,446,998 | A | 8/1948 | Burk | 208/108 |
| 2,766,301 | A | 10/1956 | Buchner et al. | 585/276 |
| 3,053,907 | A | 9/1962 | Smith et al. | 568/941 |
| 3,891,684 | A | 6/1975 | Jung | 260/429 |
| 3,903,120 | A | 9/1975 | Shook, Jr. et al. | 260/439 |
| 3,997,579 | A | 12/1976 | Jesson et al. | 260/439 |
| 5,216,186 | A | 6/1993 | Sunagawa et al. | 556/21 |
| 5,523,437 | A | 6/1996 | Hayashi et al. | 556/21 |
| 5,831,107 | A | 11/1998 | Beller et al. | 556/16 |
| 6,043,387 | A | 3/2000 | Pye et al. | 556/21 |
| 6,084,114 | A | 7/2000 | Geissler et al. | 556/21 |
| 6,124,476 | A | 9/2000 | Guram et al. | 549/200 |
| 6,291,722 | B1 | 9/2001 | Li | 568/642 |
| 6,670,645 | B2 | 12/2003 | Grushin et al. | 257/98 |
| 2003/0069373 | A1 | 4/2003 | Holtcamp et al. | 526/170 |
| 2003/0085646 | A1 | 5/2003 | Takiguchi et al. | 313/463 |

FOREIGN PATENT DOCUMENTS

| WO | WO 00/50470 | 8/2000 |
|---|---|---|
| WO | WO 02/02714 A2 | 1/2002 |
| WO | WO 03/013723 A1 | 2/2003 |
| WO | WO 03/035796 A1 | 5/2003 |
| WO | WO 03/040257 A1 | 5/2003 |
| WO | WO 03/063555 A1 | 7/2003 |

OTHER PUBLICATIONS

Couve-Bonnaire, S. et al.: Palladium-catalyzed carbonylative coupling of pyridine halides with aryl boronic acids. Tetrahedron, vol. 59, pp. 2793-2799, 2003.*
Emsley, J., "Suzuki takes the Fast Lane-and Delivers Impressive Results", What's ot in Chemistry, *ScienceWatch*, Sep. /Oct. 2001, http://www.sciencewatch.com/sept-oct2001/sw_sept-oct2001_page5.htm, 3 pages.
Goerlich, J. et al., "DI-1-Adamanthylphosphin, Ein Sterisch Hoch Gehindertes Sekundäres Phosphin. Darstellung und Reaktionen", *Phosphorus, Sulfur, and Silicon*, 1993, 81, 141-148.
No, B.I. et al., "Phosphonous Dichlorides and Phosphinic Chlorides Containing Adamantane Fragments", *Volgograd Polytechnic Institute translated from Zhurnal Obshchei Khimii*, 1990, 60(8),1795-1799.
Littke, A.F. et al., "Versatile Catalysts for the Suzuki Cross-Coupling of Arylboronic Acids with Aryl and Vinyl Halides and Triflates under Mild Conditions", *J. Am. Chem. Soc.*, 2000, 122, 4020-4028.
Miura, Y. et al., "A Convenient and Efficient Synthesis of Polyphenylmono-, -di-, and -Triaminobenzenes", *Synthesis*, 1995, 1419-1422.
Miura, Y. et al., "Pyridyl-Substituted Thioaminyl Stable Free Radicals: Isolation, ESR Spectra, and Magnetic Characterization", *J. Org. Chem*, 1998, 63, 8295-8303.
Schmid, M. et al., "New C2v-and Chiral C2-Symmetric Olefin polymerization Catalysts Based on Nickel (II) and Palladium (II) Diimine Complexes Bearing 2,6-Diphenyl Aniline Moieties: Synthesis, Structural Characterization, and First Insight into Polymerization Properties", *Organometallics*, 2001, 20, 2321-2330.
Ionkin, A.S. et al., "Synthesis and Structural Charcaterization of n3-allyl (Alpha-Diimine) Nickel Complexes Bearing Trimethylsilyl Gorups", *J. of Organomettalic Chem*, 2004, 689, 1057-1063.
DeVasher, R.B. et al., "Aqueous-Phase, Palladium-Catalyzed Cross-Coupling of Aryl Bromides under Mild Conditions, Using Water-Soluble, Sterically Demanding Alkylphosphines", *J. Org. Chem.*, 2004, 69, 7919-7927.
Smith, R.C. et al., "Suzuki Reactions Catalyzed by Palladium Complexes Bearing the Bulky (2,6-Dimesitylphenyl) dimethylphospohine", *Tetrahedron Lett*, 2004, 45, 8327-8330.

* cited by examiner

*Primary Examiner* — Charanjit Aulakh
(74) *Attorney, Agent, or Firm* — Woodcock Washburn LLP

(57) ABSTRACT

The present invention relates to a new method of cross-coupling aryl moieties comprising reacting an arylhalide with an arylboronic acid in the presence of a palladium compound and a compound comprising a di-alkylphosphine moiety.

12 Claims, No Drawings

CATALYSTS USEFUL FOR CATALYZING THE COUPLING OF ARYLHALIDES WITH ARYLBORONIC ACIDS

CROSS-REFERENCE TO RELATED APPLICATIONS

This application is a divisional of U.S. patent application Ser. No. 11/013,679, filed Dec. 16, 2004, now allowed, which is herein incorporated by reference in its entirety.

FIELD OF THE INVENTION

The present invention is directed to the field of palladium catalyzed cross-coupling reactions.

BACKGROUND OF THE INVENTION

There has been a great deal of attention directed towards the elaboration of organic compounds from readily available building blocks. One reason for such attention relates to the synthesis of pharmaceutical molecules, synthetic polymers, pesticides, food supplements, and a host of other, useful materials. Moreover, the preparation of electronics chemicals can benefit greatly from improved synthetic schemes. Of particular importance is the coupling of compounds between their respective carbon atoms, which is an important tool for synthesizing and building organic compounds. The coupling of compounds is usually complicated due to sensitivity of different functional groups on the compounds to the reaction conditions or catalysts. While some methods for coupling compounds are available, they do not always offer the efficiencies or economies required for large scale production and are not appropriate for all syntheses. Accordingly, there is continuing interest in improving methods of synthesis involving carbon-carbon coupling, called cross-coupling when between different organic molecules.

The art of cross-coupling reactions catalyzed by palladium catalysts is a powerful method to combine organic molecules by joining their carbon atoms. In the Suzuki cross-coupling reaction, carbon atoms of a boronic acid and an aryl halide are coupled via palladium catalysis under basic conditions. Recently, palladium catalysts, such as Pd(PPh$_3$)$_4$, have been used with the Suzuki reaction to cross-couple an aryl or a vinyl boronic acid to an aryl or vinyl halide or triflate. Certain other palladium catalysts, like PdCl$_2$(dppf) and Pd(OAc)$_2$, are also available. Primary alkyl groups can also be transferred by the Suzuki reaction using 9-BBN reagents and PdCl$_2$(dppf) as a catalyst.

A category of palladium catalysts useful in cross-coupling reactions are palladium-phosphine complexes. In one example, Sunagawa et al., U.S. Pat. No. 5,216,186, describe the synthesis of crystalline palladium tetrakis(triphenylphosphine) or Pd(PPh$_3$)$_4$. Sunagawa et al. also describe palladium tetrakis(triphenylphosphine) to be useful in the field of organic synthesis, explaining its use as a catalyst for deprotecting reactions of allyl esters or allyl ethers or allylation reactions of carbon or nitrogen atoms. Beller et al. in U.S. Pat. No. 5,831,107 describe a number of palladacycles and their importance as catalysts for processes such as the synthesis of substituted styrenes, preparation of stilbenes and cinnamic acids from aryl halides.

Despite the usefulness of palladium-phosphine complexes and their use in cross-coupling reactions, the use of phosphine ligands often can result in side reactions such as phosphonium salt formation and aryl-aryl exchange between substrate and phosphine. In addition, it is known that highly sensitive compounds often do not tolerate the basic conditions required by the Suzuki reaction. Also, this reaction requires extensive refluxing of the reaction mixtures. Furthermore, a popular phosphine catalyst, tri-tert-butylphosphine is known to be very expensive and may not be practicable for large scale production of materials.

Accordingly, there still remains a need for an economical, selective and efficient means for cross-coupling of compounds, particularly aryl compounds, via their respective carbon atoms. Further, there is a need for an economical, selective and efficient cross-coupling reaction that provides mild conditions for the synthesis of aryl derivates such as arylpyridines and aryl anilines, particularly sterically hindered ortho-substituted anilines.

SUMMARY OF THE INVENTION

In accordance with one aspect of the present invention, there are provided methods for cross-coupling aryl moieties by reacting an arylhalide with an arylboronic acid moiety. This reaction is catalyzed by the presence of a palladium compound in combination with a compound that includes a di-alkylphosphine moiety. The di-alkylphosphine moiety has the following formula: $(R^1)_2X—R^2$. Group X is either P or P=O; $R^1$ is a bulky alkyl; and $R^2$ is either H, alkyl, arylalkyl, or fused polyaromatic group.

The foregoing general description and the following detailed description are exemplary and explanatory only and are not restrictive of the invention, as defined in the appended claims.

DETAILED DESCRIPTION OF ILLUSTRATIVE EMBODIMENTS

In accordance with one aspect of the present invention, there are provided methods for cross-coupling aryl moieties by reacting an arylhalide with an arylboronic acid moiety. This reaction is catalyzed by the presence of a palladium compound in combination with a compound that includes a di-alkylphosphine moiety. The di-alkylphosphine compound has the following formula: $(R^1)_2X—R^2$. Group X is either P or P=O; $R^1$ is the same or different at each occurrence and is a bulky alkyl; and $R^2$ is H, alkyl, arylalkyl, or a fused polyaromatic group.

The term "bulky alkyl" is a subclass of "alkyl" that is further defined by having a large three-dimensional size; thereby, as a group bound to a central phosphorus atom, the "bulky alkyl" occupies a large steric region around the phosphorus atom. Such bulky alkyl groups present a steric hindrance to the central atom. Examples of bulky alkyl groups include, but are not limited to, tert-butyl, adamantyl, and neopentyl moieties, which may be further substituted.

In one embodiment, the two $R^1$ groups are the same. In one embodiment, the di-alkylphosphine compound is selected from di-tert-butylphosphines, di-adamantyl phosphines, and di-neopentyl phosphines.

In one embodiment, $R^2$ is selected from 2,2-dimethylpropyl, benzyl, trimethylsilanylmethyl, and pyrenyl.

In one embodiment, the cross-coupled aryl moieties are pyridines, anilines, or similar species. There are provided methods of preparing an aryl pyridine, aryl aniline or the like, comprising reacting an ortho halopyridine or ortho haloaniline with an aryl boronic acid in the presence of palladium and either di-tert-butylphosphine or di-adamantyl phosphine. Where the aryl moiety is pyridine, the cross-coupling methods produce aryl pyridines. The pyridines can be ortho-substituted and, additionally, the pyridine can also be substituted at each of the 2 and 4 positions on the pyridine, and elsewhere. In particular embodiments of the present invention, the cross-coupled aryl moiety produced by the described methods is an aryl pyridine such as 2-(3,5-bis-trifluoromethyl-phenyl)-4-methyl-pyridine; 1-(4-trimethylsilanyl-phenyl)-isoquinoline; benzofuran-2-yl-4-methyl-pyridine; 2-(3-chloro-phenyl)-4-methyl-pyridine; or 5-methyl-2-(4-trimethylsilanyl-phenyl)-pyridine.

In accordance with another aspect of the invention, where the aryl moiety is aniline, the cross-coupling methods produce aryl anilines. The anilines can be ortho-substituted or ortho-di-substituted, and substituted elsewhere if desirable. The anilines can be di-substituted with aryl moieties. In other embodiments, the cross-coupled aryl moiety produced by the described methods can be arylanilines such as 5'-isopropyl-[1,1'; 3',1"]terphenyl-2'-ylamine; 4-tert-butyl-4"-tert-butyl-[1,1';3',1"]terphenyl-2'-ylamine; 2,6,2",6"-tertmethoxy-[1,1';3',1"]terphenyl-2'-ylamine; or 4,4"-Bis(trimethylsilyl)-[1,1';3',1"]terphenyl-2'ylamine.

The present methods of cross-coupling include an arylhalide reactant. The aryl moiety includes compounds having an aromatic ring structures such as benzene, naphthalene, phenanthrene, anthracene, and fluorene or hetero-aromatic ring structures such as pyridine, pyran, pyrimidine, and indole, and derivatives thereof that keep the aromatic ring intact. Additionally, the arylhalide is characterized by a halide bound to the aryl compound, especially iodide, bromide or chloride. Also, the halide group as understood by the methods of the present invention also can be halide equivalents such as triflate. In some embodiments of the present invention, the methods include an aryl halide that is selected from 2-chloro-4-methyl-pyridine; 1-chloro-isoquinoline; 2-bromo-4-methyl-pyridine; 2-bromo-5-methyl-pyridine; 2,6-dibromo-4-isopropyl-phenylamine; and 2,6-dibromo-phenylamine.

The present methods of cross-coupling include an arylboronic acid. The arylboronic acid may be a —B(OH)$_2$ group substituent. In one embodiment, the arylboronic acid that is selected from 3,5-bis-trifluoromethyl-phenylboronic acid; 2-benzofuranboronic acid; 3-chlorophenylboronic acid; 4-trimethylsilyl-butylphenylboronic acid; phenylboronic acid; 4-tert-butylphenylboronic acid; and 2,6-dimethoxyphenylboronic acid.

The present methods include cross-coupling reactions catalyzed in part by the presence of palladium. The palladium is contemplated to be a palladium complex. Examples of palladium complexes include, but are not limited to, PdCl$_2$(dppf), Pd(PPh$_3$)$_4$, Pd(OAc)$_2$, and Pd$_2$dba$_3$, where dppf is 1,1 bis(diphenyl phosphino)ferrocene, Ph is phenyl, OAc is acetate, and dba is dibenzylideneacetone. Other palladium complexes known to be useful in similar type cross-coupling reactions are also contemplated within the scope of the present invention.

In one embodiment, the dialkyl-phosphine is a di-tert-butylphosphine and R$^2$ is a mono-substituted methylene group. In one embodiment, the di-tert-butylphosphine is selected from benzyl-di-tert-butyl-phosphine; di-tert-butyl-(2,2-dimethyl-propyl)-phosphine; di-tert-butyl-trimethylsilanylmethyl-phosphine; (di-tert-butyl-phosphinoylmethyl)-trimethyl-silane; and di-tert-butyl-pyren-1-yl-phosphine.

In other aspects of the present invention, the dialkyl-phosphine compound is a di-adamantylphosphine compound. In particular embodiments, the di-adamantylphosphine is either di-1-adamantylphosphine oxide or di-1-adamantylmethylphosphine.

In general, di-aryl compounds are synthesized by a reaction such as that outlined in Scheme I.

Scheme I

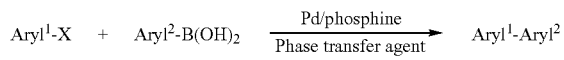

where X is a halide, Pd is a palladium compound, phosphine is a compound or complex including phosphine or phosphine oxide, and a phase transfer agent is a mild base.

The new synthetic methods provide for the synthesis of di-aryl compounds that are useful in a number of industries. The synthetic methods provide products that may consist of pharmaceutical molecules, synthetic polymers, pesticides, food supplements, and a host of other, useful materials, including organic electronic devices, e.g., OLED devices. In one embodiment, the di-aryl compounds can be used to formulate many of the layers incorporated into an organic electronic device, for example an electron transport layer. In one embodiment, the di-aryl compounds can be used as ligands to form cyclometallated organometallic complexes. Such cyclometallated complexes can be light-emitting. Cyclometallated iridium complexes have been disclosed in, for example, U.S. Pat. No. 6,670,645 and published PCT applications WO 02/02714 and WO 03/063555. Cyclometallated platinum complexes have been disclosed in, for example, published PCT application WO 03/040257. These references are hereby incorporated by reference in their entirety.

In one embodiment, the products of the methods of the present invention can be used to form an organic electronic device, which includes, but is not limited to: (1) a device that converts electrical energy into radiation (e.g., a light-emitting diode, light emitting diode display, diode laser, or lighting panel), (2) a device that detects a signal using an electronic process (e.g., a photodetector, a photoconductive cell, a photoresistor, a photoswitch, a phototransistor, a phototube, an infrared ("IR") detector, or a biosensors), (3) a device that converts radiation into electrical energy (e.g., a photovoltaic device or solar cell), (4) a device that includes one or more electronic components that include one or more organic semiconductor layers (e.g., a transistor or diode), or any combination of devices in items (1) through (4). Persons of skill in the art will recognize that other organic electronic devices may be elaborated and that additional classes of such devices may arise in the future which may benefit from the present invention. All such are contemplated hereby.

DEFINITIONS

As used herein, the term "group" is intended to mean a part of a compound, such as a substituent in an organic compound or a ligand in a metal complex. Unless otherwise indicated, all groups can be unsubstituted or substituted. Unless otherwise indicated, all groups can be linear, branched or cyclic, where possible.

The prefix "hetero" indicates that one or more carbon atoms have been replaced with a different atom. The term "alkyl" is intended to mean a group derived from an aliphatic hydrocarbon having one point of attachment. The group can have from 1-20 carbon atoms.

The term "aryl" is intended to mean a group derived from an aromatic hydrocarbon having one point of attachment. The group can have from 6-30 carbon atoms. A heteroalkyl group can have from 4-30 carbon atoms. The term "arylene" is intended to mean a group derived from an aromatic hydrocarbon having two points of attachment.

The term "arylalkylene" is intended to mean a group derived from an alkyl group having an aryl substituent.

The term "di-alkylphosphine" refers to a compound having two alkyl group bonded to a single phosphorus atom.

The term "arylhalide" means an aromatic compound having a "halide" substituent, or a plurality of halide substituents.

The term "arylboronic acid" means an aromatic compound having a "boronic acid" substituent. The "boronic acid" means a —B(OH)$_2$ moiety bound to the aryl.

The term "halogen" or "halide" includes fluorine, chlorine, iodine, and bromine. Additionally, the halide group as understood by the methods of the present invention also can be halide equivalents such as triflate.

The term "adamantyl" means a cyclical alkyl having the empirical formula $C_{10}H_{15}$ and has a structure consisting of four fused cyclohexane rings.

The term "ortho" or "ortho-substituted" means a position on a ring structure that is the next position on the ring from the reference position. For example, 2-chloroaniline is characterized by a chloro substitutent on a phenyl moiety positioned ortho to the amino substituent.

The term "phase transfer agent" means a mild base that assists the palladium-catalyzed cross-coupling between two compounds, both having aryl moieties. The base may be CsF, $Cs_2CO_3$, tetra-alkylammonium hydroxide, tetra-alkylammonium chloride, or another mild base having similar basic strength and reactive characteristics.

The term "fused polyaromatic group" means a group having two or more fused aromatic rings.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

The following examples illustrate certain features and advantages of the present invention. They are intended to be illustrative of the invention, but not limiting. All percentages are by weight, unless otherwise indicated.

Examples 1-5 provide methods for the synthesis of compounds having a di-tert-butylphosphine moiety. Examples 6 and 7 provide methods for the synthesis of compounds having a di-adamantylphosphine moiety. These compounds are useful for the catalysis of the cross-coupling reactions described herein.

Example 1

This example illustrates the preparation of benzyl-di-tert-butyl-phosphine from di-tert-butyl-chlorophosphine.

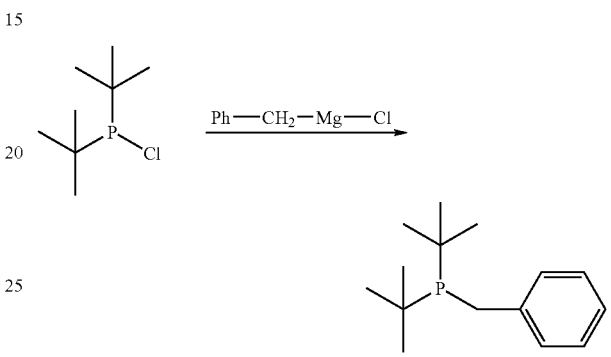

Di-t-butyl-chlorophosphine (75.0 g (0.415 mole)) and 0.5 mole of 12M solution of benzylmagnesium chloride in THF (200 ml) were refluxed under argon for 2 days. The reaction mixture was allowed to cool off to RT and an aqueous solution of ammonium chloride was added slowly. The organic phase was separated, and dried with magnesium sulfate. After removal of the solvent, the product was purified by distillation in vacuum. The yield of benzyl-di-tert-butyl-phosphine was 94.3 g (96%) with b.p. 56-59° C./0.1 mm. 31-P-NMR (CDCl3)+36.63 ppm. $^1$H NMR (CDCl$_3$) 1.18 (s, 9H, Me$_3$C), 1.20 (s, 9H, Me$_3$C), 2.90 (d, $^2J_{PH}$=2.92 Hz, P—CH$_2$-Ph), 7.1-7.6 (m, 5H, aromatic protons). Anal. Calcd. For C15H25P: C, 76.23; H, 10.66; P, 13.11. Found: C, 76.15; H, 10.58; P, 12.87.

Example 2

This example illustrates the preparation of di-tert-butyl-(2,2-dimethyl-propyl)-phosphine from di-tert-butyl-chlorophosphine.

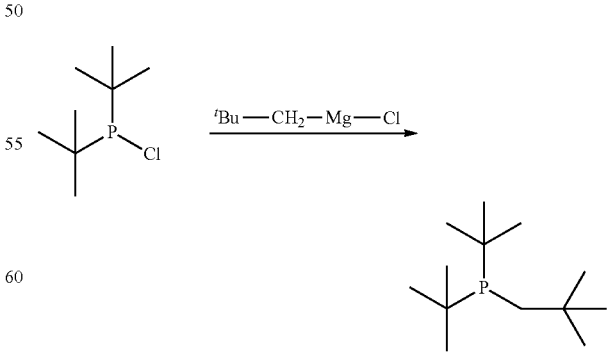

28.80 g (0.160 mol) of di-t-butyl-chlorophosphine, 0.2 mole of neopentylmagnesium chloride in diethyl ether and 150 ml of THF) were refluxed under argon for 3 days. The reaction mixture was allowed to cool off to RT and an aqueous solution of ammonium chloride was added slowly. The organic phase was separated, and dried with magnesium sulfate. After removal of the solvent, the product was purified by distillation in vacuum. The yield of di-tert-butyl-(2,2-dimethyl-propyl)-phosphine was 25.26 g (73%) with b.p. 43-47° C./0.1 mm. 31-P-NMR (CD$_2$Cl$_2$)+19.76 ppm. $^1$H NMR (CD$_2$Cl$_2$) 1.17 (s, 9H, Me$_3$C), 1.19 (s, 9H, Me$_3$C), 2.47 (d, $^2$J$_{PH}$=3.12 Hz, P—CH$_2$—CMe$_3$). Anal. Calcd. for C13H29P: C, 72.17; H, 13.51; P, 14.32. Found: C, 72.01; H, 13.49; P, 14.08.

Example 3

This example illustrates the formation of di-tert-butyl-trimethylsilanylmethyl-phosphine from di-tert-butyl-chlorophosphine.

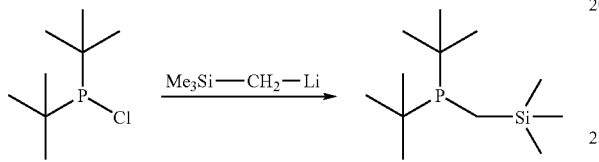

50.00 g (0.277 mol) of di-t-butylchlorophosphine, 304 ml of 1.0 M pentane solution of (trimethylsilylmethyl)lithium and 150 ml of THF) were refluxed under argon for 3 days. The reaction mixture was allowed to cool off to RT and an aqueous solution of ammonium chloride was added slowly. The organic phase was separated, and dried with magnesium sulfate. After removal of the solvent, the product was purified by distillation in vacuum. The yield of di-tert-butyl-trimethylsilanylmethyl-phosphine was 55.32 g (86%) with b.p. 50-52° C./0.5 mm. 31-P-NMR (C$_6$D$_6$)+20.05 ppm. $^1$H NMR (C$_6$D$_6$) 0.01 (s, 9H, SiMe$_3$), 0.23 (d, 2H, $^2$J$_{PH}$=5.34 Hz, P—CH$_2$—SiMe$_3$), 0.91 (s, 9H, Me$_3$C), 0.93 (s, 9H, Me$_3$C). Anal. Calcd. for C12H29PSi: C, 62.01; H, 12.58; P, 13.33. Found: C, 61.89; H, 12.53; P, 13.25. Di-tert-butyl-trimethylsilanylmethyl-phosphine was oxidized by the oxygen of air with the formation of the corresponding oxide.

Example 4

This example shows the formation of (di-tert-butyl-phosphinoylmethyl)-trimethyl-silane from di-tert-butyl-trimethylsilanylmethyl-phosphine.

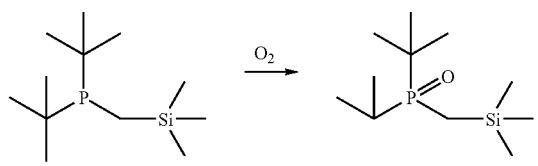

1.0 g (0.0043 mol) of di-tert-butyl-trimethylsilanylmethyl-phosphine was exposed to air for 3 hours. Then resulted waxy solid was recrystallized from chloroform. Yield of (di-tert-butyl-phosphinoylmethyl)-trimethyl-silane was 0.82 g (77%) with m.p. 75.64° C. 31-P-NMR (CDCl$_3$)+62.73 ppm. $^1$H NMR (CDCl$_3$) 0.00 (s, 9H, SiMe$_3$), 0.87 (d, 2H, $^2$J$_{PH}$=10.0 Hz, P(O)—CH$_2$—SiMe$_3$), 1.02 (s, 9H, Me$_3$C), 1.04 (s, 9H, Me$_3$C). Anal. Calcd. for C12H29OPSi: C, 58.02; H, 11.77; P, 12.47. Found: C, 57.86; H, 11.75; P, 12.31. The structure has been proved by X-ray analysis.

Example 5

This example illustrates the preparation of di-tert-butyl-pyren-1-yl-phosphane from di-tert-butyl-chlorophosphine.

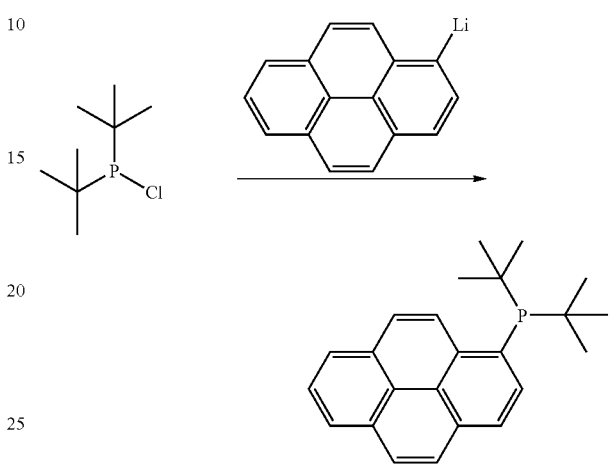

24.0 g (0.085 mol) of 1-Bromopyrene was dissolved in 240 ml of THF. The reaction mixture was cooled to −78° C. and 64 ml of 1 M solution of Butyllithium in hexanes was added dropwise. 18.50 g (0.10 mol) of di-t-butyl-chlorophosphine was added in the resultant mixture after warming it up to ambient temperature. Then, the mixture was stirred for 3 days at RT and diluted with 200 ml of the water under nitrogen. The organic phase was separated, and dried with magnesium sulfate. After removal of the solvent, the product was purified by kugehrohr distillation at 120° C./0.01 mm. The yield of di-tert-butyl-pyren-1-yl-phosphane was 8.14 g (27.53%) with m.p. 97.07° C. 31-P-NMR (C$_6$D$_6$)+28.36 ppm. $^1$H NMR (C$_6$D$_6$) 1.43 (d, $^3$J$_{PH}$=11.8 Hz, 18H, Me$_3$C), 7.60-10.00 (m, 9H, Arom-H). Anal. Calcd. for C24H27P (Mol. Wt.: 346.44): C, 83.20; H, 7.86; P, 8.94. Found: C, 83.17; H, 7.96; P, 9.14. The structure was proved by X-ray analysis.

Example 6

This example shows di-1-adamantylmethylphosphine being formed from di-1-adamantylphosphinic chloride in two steps. The first or intermediate step results in the formation of di-1-adamantylmethylphosphine oxide.

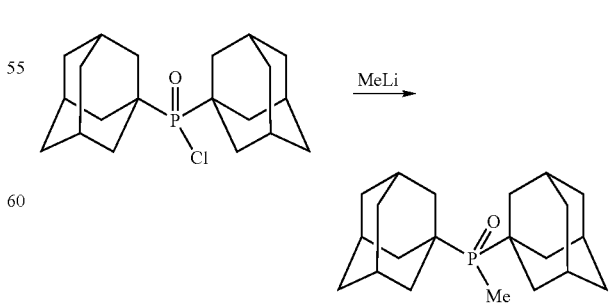

30.0 g (0.0852 mol) of di-1-adamantylphosphinic chloride, 73 ml of 1.4M solution of methyllithium in diethyl ether and 400 ml of THF were stirred at room temperature for 1 week. The reaction mixture slowly hydrolyzed and extracted in chloroform. The organic fraction was dried under magnesium sulfate, and filtered. The residue was recrystallized from hexanes. Yield of di-1-adamantylmethylphosphine oxide was 24.46 g (86%). 31-P-NMR (CDCl₃)+52.86 ppm. Lit. 31-P-NMR (CDCl₃)+52.72 ppm. (J. Goerlich, R. Schmutzler. Phosphorus, Sulfur, and Silicon, 1993, vol. 81, 141-148.)

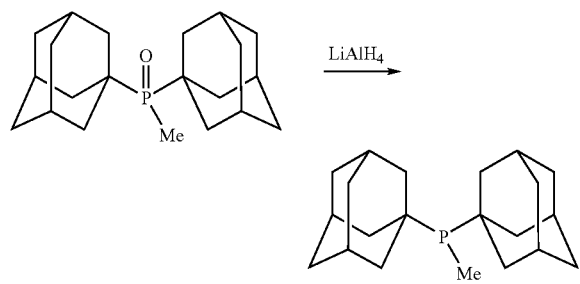

20.0 g (0.060 mol) of di-1-adamantylmethylphosphine oxide, 4.5 g (0.118 mol) of lithium aluminum hydride and 450 ml of THF were refluxing for 2 hours. Then the reaction mixture was cooled and slow hydrolyzed under argon. The organic phase was dried under degassed magnesium sulfate. The residue after evaporation of solvent was recrystallized from pentane. Yield of di-1-adamantylmethylphosphine was 6.78 g (36%). 31-P-NMR (CDCl₃)+7.02 ppm. Lit. 31-P-NMR (CDCl₃)+7.99 ppm. (J. Goerlich, R. Schmutzler. Phosphorus, Sulfur, and Silicon, 1993, vol. 81, 141-148.)

Example 7

This example illustrates the formation of di-1-adamantylphosphine oxide from di-1-adamantylphosphinic chloride in two steps, the first step resulting in the formation of di-1-adamantylphosphine.

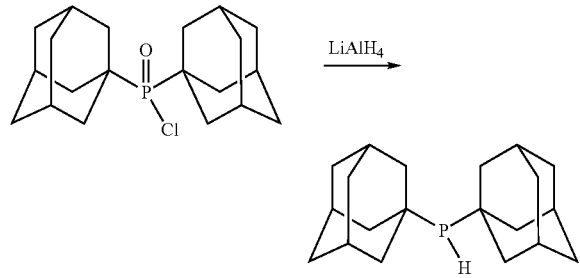

Di-1-adamantylphosphinic chloride was prepared according the literature, see procedure: B. I. No, Yu. L. Zotov, V. N. Karev. Zh. Obshch. Khim., 60, 1795 (1990). 31-P-NMR (CDCl₃)+87.19 ppm. ¹H NMR (CDCl₃) 1.77-2.31 (m, 30H, C₁₀H₁₅). The structure was proved by X-ray spectroscopy.

Di-1-adamantylphosphine was prepared according the literature, see procedure: B. I. No, Yu. L. Zotov, V. N. Karev. Zh. Obshch. Khim., 60, 1795 (1990). 31-P-NMR (CDCl₃)+19.44 ppm. Di-1-adamantylphosphine oxide was prepared as well according the literature, see procedure: B. I. No, Yu. L. Zotov, V. N. Karev. Zh. Obshch. Khim., 60, 1795 (1990). 31-P-NMR (CDCl₃)+60.32 ppm ($^1J_{PH}$=430.4 Hz).

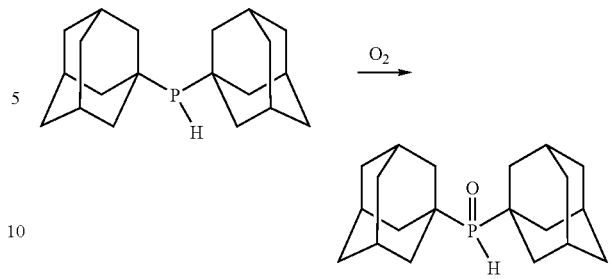

The following examples provide methods for cross-coupling aryl moieties through a palladium catalyzed reaction. Examples 7-10 provide methods for cross-coupling a compound having a pyridine moiety with an arylboronic acid. Whereas, Examples 11-15 provide methods for cross-coupling a compound having an aniline moiety with an arylboronic acid.

Example 8

This example illustrates the formation of 2-(3,5-Bis-trifluoromethyl-phenyl)-4-methyl-pyridine.

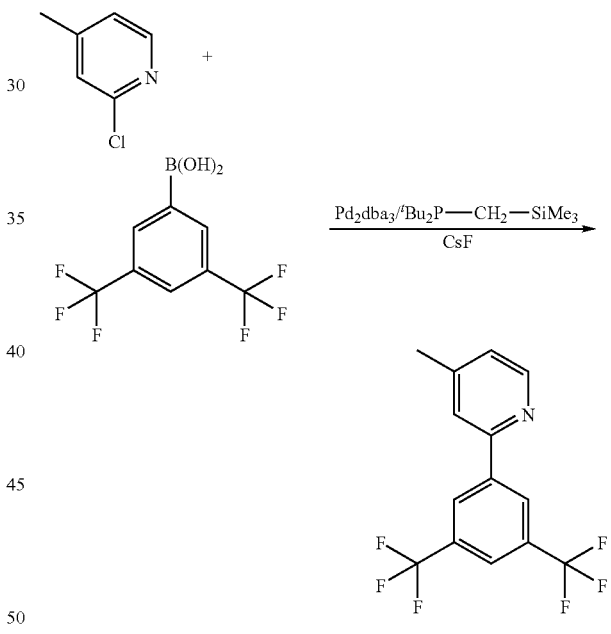

15.0 g (0.05815 mol) of 3,5-bis-trifluoromethyl-phenylboronic acid, 7.42 g (0.05816 mol) of 2-chloro-4-methyl-pyridine, 17.43 g (0.1148 mol) of cesium fluoride, 0.53 g (0.000579 mol) of tris(dibenzylideneacetone) dipalladium (0), 0.33 g (0.00142 mol) of di-tert-butyl-trimethylsilylmethyl-phosphine and 100 ml of dioxane were stirred at room temperature for 12 hours. The reaction mixture was filtered and the solvent was removed under vacuum. The resulting mixture was purified by chromatography on silica gel with eluent petroleum ether/ethyl ether at 10/0.5. Yield of 2-(3,5-bis-trifluoromethyl-phenyl)-4-methyl-pyridine was 16.18 g (91%) as colorless liquid. ¹H NMR (CDCl₃) 2.56 (s, 3H, Me), 7.11 (s, 1H, arom-H), 7.51 (s, 1H, arom-H), 7.90 (s, 1H, arom-H), 8.45-8.55 (m, 3H, arom-H). ¹⁹F NMR (CDCl₃)–63.35, −63.36 (1:1). Anal. Calcd. for C14H9F6N: C, 55.09; H, 2.97; N, 4.59. Found: C, 55.01; H, 3.12; N, 4.44.

Example 9

In this example, 1-(4-trimethylsilanyl-phenyl)-isoquinoline is synthesized from 1-chloro-isoquinoline and 4-trimethylsilyl-butylphenylboronic acid.

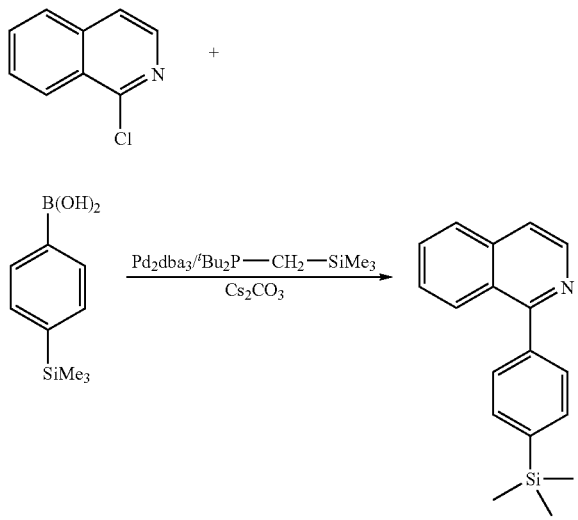

15.0 g (0.07727 mol) of 4-trimethylsilyl-butylphenylboronic acid, 10.11 g (0.0618 mol) 1-chloro-isoquinoline, 15.11 g (0.0464 mol) of cesium carbonate, 0.71 g (0.000775 mol) of tris(dibenzylideneacetone) dipalladium (0), 0.43 g (0.00185 mol) of di-tert-butyl-trimethylsilylmethyl-phosphine and 100 ml of dioxane were stirred at room temperature for 12 hours. The reaction mixture was filtered and the solvent was removed under vacuum. The resulting mixture was purified by chromatography on silica gel with eluent petroleum ether/ethyl ether at 10/0.5. Yield of 1-(4-trimethylsilanyl-phenyl)-isoquinoline was 10.63 g (62%) as colorless solid with m.p. 93.45° C. $^1$H NMR (CDCl$_3$) 0.30 (s, 9H, Me$_3$Si), 7.45-7.70 (m, 7H, arom-H), 7.85 (s, 1H, arom-H), 8.15 (s, 1H, arom-H), 8.51 (s, 1H, arom-H). Anal. Calcd. for C18H19NSi: C, 77.93; H, 6.90; N, 5.05. Found: C, 77.68; H, 6.95; N, 4.97.

Example 10

This example illustrates the formation of benzofuran-2-yl-4-methyl-pyridine.

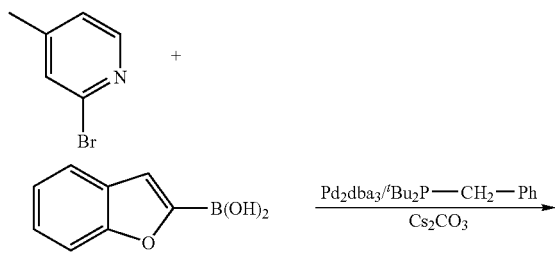

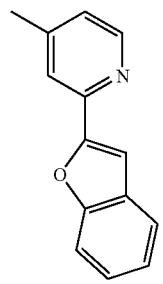

16.0 g (0.0988 mol) of 2-benzofuranboronic acid, 13.0 g (0.0756 mol) of 2-bromo-4-methyl-pyridine, 18.00 g (0.0553 mol) of cesium carbonate, 0.90 g (0.000983 mol) of tris(dibenzylideneacetone) dipalladium (0), 0.56 g (0.00237 mol) of benzyl-di-tert-butyl-phosphine and 100 ml of dioxane were stirred at room temperature for 12 hours. The reaction mixture was filtered and the solvent was removed under vacuum. The resulting mixture was purified by chromatography on silica gel with eluent petroleum ether/ethyl ether at 10/2.0. Yield of benzofuran-2-yl-4-methyl-pyridine was 10.61 g (67%) as colorless solid with m.p. 92.72° C. $^1$H NMR (CDCl$_3$) 2.12 (s, 3H, Me) 5.95-8.55 (m, 8H, arom-H). Anal. Calcd. for C14H11NO: C, 80.36; H, 5.30; N, 6.69. Found: C, 80.23; H, 5.19; N, 6.79. The structure has been confirmed by X-ray analysis.

Example 11

In this example, a method of forming 5-methyl-2-(4-trimethylsilanyl-phenyl)-pyridine is shown.

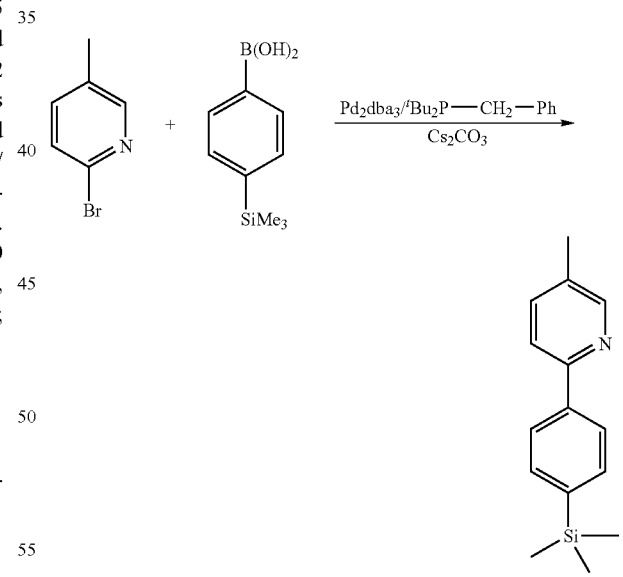

15.0 g (0.0773 mol) of 4-trimethylsilyl-butylphenylboronic acid, 11.96 g (0.0695 mol) of 2-bromo-5-methyl-pyridine, 15.11 g (0.0464 mol) of cesium carbonate, 0.71 g (0.000776 mol) of tris(dibenzylideneacetone) dipalladium (0), 0.43 g (0.00182 mol) of benzyl-di-tert-butyl-phosphine and 100 ml of dioxane were stirred at room temperature for 12 hours. The reaction mixture was filtered and the solvent was removed under vacuum. The resulting mixture was purified by distillation in vacuum. Yield of 5-methyl-2-(4-trimethylsilanyl-phenyl)-pyridine was 8.05 g (48%) as yellow solid with b.p. at 111-114° C./0.02 mm and m.p. 66.07° C. $^1$H NMR (CD$_2$Cl$_2$) 2.15 (s, 3H, Me) 7.45-8.50 (m, 7H, arom-H). Anal. Calcd. for C15H19NSi: C, 74.63; H, 7.93; N, 5.80. Found: C, 74.34; H, 7.86; N, 5.85. The structure has been confirmed by X-ray analysis.

Example 12

This example illustrates the preparation of 2-(3-chlorophenyl)-4-methyl-pyridine.

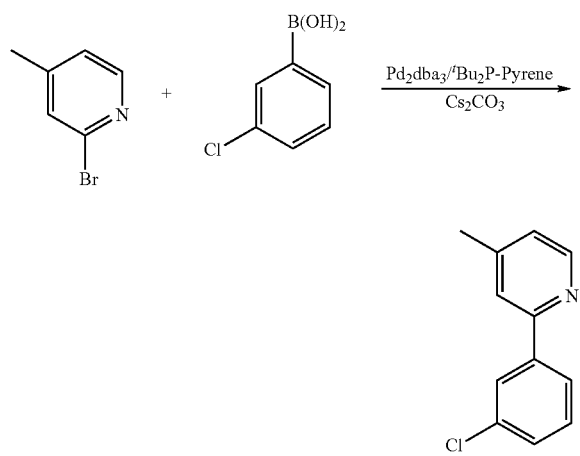

10.0 g (0.064 mol) of 3-Chlorophenylboronic acid, 13.20 g (0.077 mol) of 2-bromo-5-methyl-pyridine, 20.84 g (0.064 mol) of cesium carbonate, 1.47 g (0.0016 mol) of tris(dibenzylideneacetone) dipalladium (0), 1.33 g (0.0038 mol) of di-tert-butyl-pyren-1-yl-phosphane and 100 ml of dioxane were refluxed at room for 12 hours. The reaction mixture was filtered and the solvent was removed under vacuum. The resulting mixture was purified by distillation in vacuum. Yield of 2-(3-chloro-phenyl)-4-methyl-pyridine was 7.09 g (45%) with b.p. at 114° C./0.1 mm. $^1$H NMR (CD$_2$Cl$_2$) 2.56 (s, 3H, Me) 7.40-8.80 (m, 7H, arom-H). Anal. Calcd. for C12H10ClN (Mol. Wt.: 203.67): C, 70.77; H, 4.95; N, 6.88. Found: C, 70.93; H, 5.14; N, 6.95. The structure has been confirmed by X-ray analysis.

Example 13

In this example, 5'-isopropyl-[1,1';3',1"]terphenyl-2'-ylamine is synthesized from phenylboronic acid and 2,6-dibromo-4-isopropyl-phenylamine.

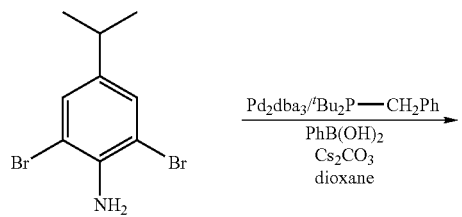

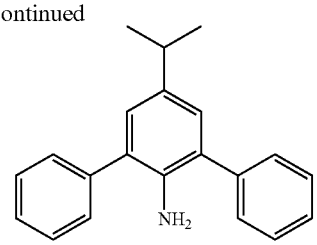

15.0 g (0.123 mol) of phenylboronic acid, 15.33 g (0.052 mol) of 2,6-dibromo-4-isopropyl-phenylamine, 48.00 g (0.147 mol) of cesium carbonate, 1.69 g (0.00185 mol) of tris(dibenzylideneacetone)dipalladium (0), 1.05 g (0.00444 mol) of benzyl-di-tert-butyl-phosphine and 125 ml of dioxane were stirred at room temperature for 12 hours. The reaction mixture was filtered and the solvent was removed under vacuum. The resulting mixture was purified by chromatography on silica gel with eluent petroleum ether/ethyl ether at 10/2. Yield of 5-isopropyl-3-penta-2,4-dienyl-biphenyl-2-ylamine was 8.73 g (58%) with m.p. 80.75° C. Anal. Calcd. for C21H21N: C, 87.76; H, 7.36; N, 4.87. Found: C, 87.57; H, 7.19; N, 4.83. GC/MS MW is 287.

Example 14

This example illustrates the formation of 4-tert-butyl-4"-tert-butyl-[1,1';3',1"]terphenyl-2'-ylamine.

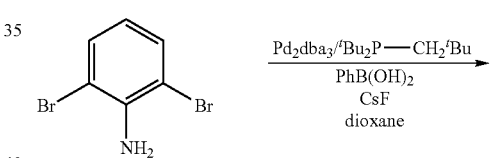

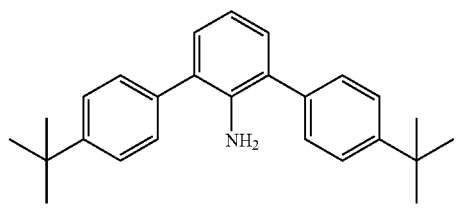

15.0 g (0.0842 mol) of 4-tert-butylphenylboronic acid, 9.51 g (0.038 mol) of 2,6-dibromo-phenylamine, 42.21 g (0.278 mol) of cesium fluoride, 0.39 g (0.000426 mol) of tris(dibenzylideneacetone)dipalladium (0), 0.27 g (0.00125 mol) of di-tert-butyl-(2,2-dimethyl-propyl)-phosphine and 125 ml of dioxane were stirred at room temperature for 12 hours. The reaction mixture was filtered and the solvent was removed under vacuum. The resulting mixture was purified by chromatography on silica gel with eluent petroleum ether/ethyl ether at 10/0.5. Yield of 4-tert-butyl-4"-tert-butyl-[1,1'; 3',1"]terphenyl-2'-ylamine was 9.08 g (67%) with m.p. 63.39° C. $^1$H NMR (CDCl$_3$) 1.30 (s, 18H, Me$_3$C), 6.31-7.50 (m, arom. 11H). Anal. Calcd. for C26H31N: C, 87.34; H, 8.74; N, 3.92. Found: C, 87.29; H, 8.63; N, 3.88. GC/MS MW is 357.

Example 15

In this example, formation of 2,6,2",6"-tetramethoxy-[1,1';3',1"]terphenyl-2'-ylamine is shown.

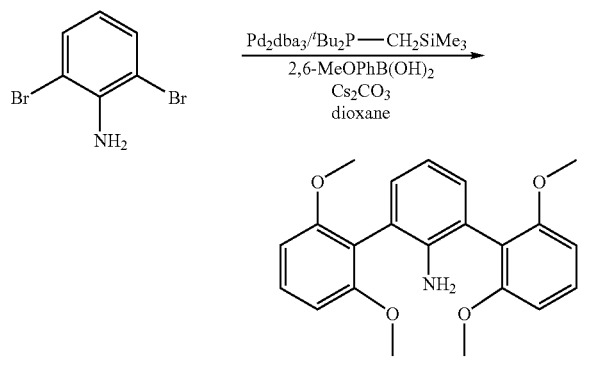

25.0 g (0.137 mol) of 2,6-dimethoxyphenylboronic acid, 11.41 g (0.046 mol) of 2,6-dibromo-phenylamine, 54.00 g (0.166 mol) of cesium carbonate, 0.62 g (0.000677 mol) of tris(dibenzylideneacetone)dipalladium (0), 0.38 g (0.00163 mol) of di-tert-butyl-trimethylsilanylmethyl-phosphine and 125 ml of dioxane were stirred at room temperature for 12 hours. The reaction mixture was filtered and the solvent was removed under vacuum. The resulting mixture was recrystallized from methylene chloride. Yield of 2,6,2",6"-tetramethoxy-[1,1';3',1"]terphenyl-2'-ylamine was 12.21 g (73%) with m.p. 177.77° C. $^1$H NMR (CDCl$_3$) 3.95 (s, 12H, MeO), 4.10 (s, 2H, NH$_2$), 6.85-7.60 (m, arom. 9H). Anal. Calcd. for C22H23NO4: C, 72.31; H, 6.34; N, 3.83. Found: C, 72.13; H, 6.28; N, 3.02. GC/MS MW is 365. The structure was confirmed by X-ray analysis.

Example 16

4,4"-bis(trimethylsilyl)-[1,1';3',1"]terphenyl-2'-ylamine is formed from 4-trimethylsilyl-butylphenylboronic acid and 2,6-dibromo-phenylamine.

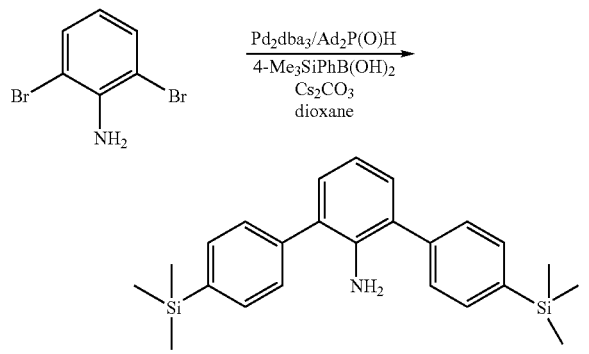

15.0 g (0.0773 mol) of 4-trimethylsilyl-butylphenylboronic acid, 6.46 g (0.026 mol) of 2,6-dibromo-phenylamine, 30.21 g (0.086 mol) of cesium carbonate, 0.37 g (0.00040 mol) of tris(dibenzylideneacetone)dipalladium (0), 0.37 g (0.00116 mol) di-1-adamantylphosphine oxide and 125 ml of dioxane were refluxed for 1 hour. The reaction mixture was cooled to room temperature, was filtered and the solvent was removed under vacuum. The resulting mixture was purified by chromatography on silica gel with eluent petroleum ether/ethyl ether at 10/0.5. Yield of 4,4"-bis(trimethylsilyl)-[1,1';3',1"]terphenyl-2'-ylamine was 4.79 g (48%) with m.p. 92.44° C. $^1$H NMR (CDCl$_3$) 0.10 (s, 18H, Me$_3$Si), 3.75 (s, 2H, NH$_2$), 6.66-7.45 (m, arom. 11H). Anal. Calcd. for C24H31NSi2: C, 73.97; H, 8.02; N, 3.59. Found: C, 74.18; H, 7.95; N, 3.50. GC/MS MW is 389. The structure was proved by X-ray analysis.

Example 17

This example illustrates an alternate method for the formation of 4,4"-bis(trimethylsilyl)-[1,1';3',1"]terphenyl-2'-ylamine.

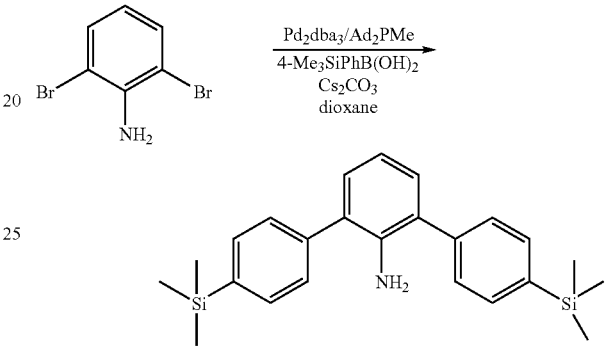

15.0 g (0.0773 mol) of 4-trimethylsilyl-butylphenylboronic acid, 6.46 g (0.026 mol) of 2,6-dibromo-phenylamine, 30.21 g (0.086 mol) of cesium carbonate, 0.37 g (0.00040 mol) of tris(dibenzylideneacetone)dipalladium (0), 0.37 g (0.00117 mol) di-1-adamantylmethylphosphine and 125 ml of dioxane were refluxed for 1 hour. The reaction mixture was cooled to room temperature, was filtered and the solvent was removed under vacuum. The resulting mixture was purified by chromatography on silica gel with eluent petroleum ether/ethyl ether at 10/0.5. Yield of 4,4"-bis(trimethylsilyl)-[1,1';3',1"]terphenyl-2'-ylamine was 0.66 g (7%) with m.p. 92.44° C. $^1$H NMR (CDCl$_3$) 0.10 (s, 18H, Me$_3$Si), 3.75 (s, 2H, NH$_2$), 6.66-7.45 (m, arom. 11H). GC/MS MW is 389.

It is to be appreciated that certain features of the invention which are, for clarity, described above in the context of separate embodiments, may also be provided in combination or in a single embodiment. Conversely, various features of the invention that are, for brevity, described in the context of a single embodiment, may also be provided separately or in any subcombination. Further, reference to values stated in ranges include each and every value within that range.

What is claimed:

1. A method of cross-coupling aryl and heteroaryl moieties to produce an aryl heteroaryl compound, said method comprising reacting a heteroarylhalide with an arylboronic acid in the presence of a palladium compound and a compound comprising a di-alkylphosphine, wherein the di-alkylphosphine has the formula:

$(R^1)_2X$—$R^2$, wherein
X is P or P=O;
$R^1$ is an adamantyl; and
$R^2$ is H, alkyl, arylalkyl, or a fused polyaromatic group.

2. A method of cross-coupling aryl and heteroaryl moieties to produce an aryl heteroaryl compound, said method comprising reacting a heteroarylhalide with an arylboronic acid in the presence of a palladium compound and a compound comprising a di-alkylphosphine, wherein the di-alkylphosphine has the formula:

$(R^1)_2X—R^2$, wherein

X is P or P=O;

$R^1$ is independently, a bulky alkyl; and $R^2$ is benzyl, 2,2-dimethyl-propyl, —(CH$_3$)$_3$Si—CH$_2$—, or pyren-1-yl.

3. The method of claim 2, wherein the di-alkylphosphine is benzyl-di-tert-butyl-phosphine; di-tert-butyl-(2,2-dimethyl-propyl)-phosphine; di-tert-butyl-trimethyl silanylmethyl-phosphine; (di-tert-butyl-phosphinoylmethyl)-trimethyl-silane; or di-tert-butyl-pyren-1-yl-phosphane.

4. The method of claim 1, wherein the di-adamantylphosphine is di-1-adamantylphosphine oxide or di-1-adamantyl-methylphosphine.

5. The method of claim 1, wherein the heteroarylhalide is a pyridinyl halide.

6. The method of claim 5, wherein the pyridinyl halide is halo-substituted at the ortho-position relative to the pyridinyl nitrogen.

7. The method of claim 1, wherein the method produces a 2-(3,5-bis-trifluoromethyl-phenyl)-4-methyl-pyridine; 1-(4-trimethylsilanyl-phenyl)-isoquinoline; benzofuran-2-yl-4-methyl-pyridine; 2-(3-chloro-phenyl)-4-methyl-pyridine; or 5-methyl-2-(4-trimethylsilanyl-phenyl)-pyridine.

8. The method of claim 1, wherein the aryl heteroaryl compound is an aryl pyridine compound.

9. A method of cross-coupling aryl and heteroaryl moieties comprising reacting a heteroarylhalide with an arylboronic acid in the presence of a palladium compound and a compound comprising a di-alkylphosphine, wherein the di-alkylphosphine has the formula:

$(R^1)_2X—R^2$, wherein

X is P or P=O;

$R^1$ is, independently, adamantyl or neopentyl; and $R^2$ is H, alkyl, arylalkyl, or a fused polyaromatic group.

10. The method of claim 9, wherein the di-alkylphosphine is di-adamantyl phosphine.

11. The method of claim 10, wherein the di-adamantylphosphine is di-1-adamantylphosphine oxide or di-1-adamantylmethylphosphine.

12. A method of cross-coupling aryl and heteroaryl moieties comprising reacting a heteroarylhalide with an arylboronic acid in the presence of a palladium compound and a compound comprising a di-alkylphosphine, wherein the di-alkylphosphine has the formula:

$(R^1)_2X—R^2$, wherein

X is P or P=O;

$R^1$ is, independently, a bulky alkyl; and $R^2$ is mono-substituted methylene.

* * * * *